United States Patent
Irnich et al.

(10) Patent No.: US 9,624,621 B2
(45) Date of Patent: Apr. 18, 2017

(54) PROCESS FOR THE PRODUCTION OF COATED TEXTILES

(71) Applicant: Bayer Intellectual Property GmbH, Monheim am Rhein (DE)

(72) Inventors: Rolf Irnich, Shanghai (CN); Shaojun Yang, Shanghai (CN)

(73) Assignee: Covestro Deutschland AG, Leverkusen (DE)

( * ) Notice: Subject to any disclaimer, the term of this patent is extended or adjusted under 35 U.S.C. 154(b) by 303 days.

(21) Appl. No.: 14/353,054

(22) PCT Filed: Oct. 16, 2012

(86) PCT No.: PCT/EP2012/070481
§ 371 (c)(1),
(2) Date: Apr. 21, 2014

(87) PCT Pub. No.: WO2013/057100
PCT Pub. Date: Apr. 25, 2013

(65) Prior Publication Data
US 2015/0093565 A1    Apr. 2, 2015

(30) Foreign Application Priority Data
Oct. 21, 2011   (WO) ............... PCT/CN2011/001754

(51) Int. Cl.
*B05D 3/02* (2006.01)
*D06N 3/14* (2006.01)
(Continued)

(52) U.S. Cl.
CPC ........... *D06N 3/145* (2013.01); *C07C 227/00* (2013.01); *C08G 18/0823* (2013.01);
(Continued)

(58) Field of Classification Search
CPC ... C07C 227/00; D06M 15/564; D06M 23/04; D06N 3/14; D06N 3/145; D06N 3/0047;
(Continued)

(56) References Cited

U.S. PATENT DOCUMENTS

| 5,851,338 A | 12/1998 | Pushaw |
| 2004/0121113 A1 | 6/2004 | Mobley et al. |

(Continued)

FOREIGN PATENT DOCUMENTS

| CA | 2253119 | 5/1999 | |
| DE | 2908314 A1 * | 9/1979 | ............... D06N 3/14 |

(Continued)

OTHER PUBLICATIONS

Machine translation of the disclosure of DE 2908314.*
International Search Report for PCT/EP2012/070481 dated Dec. 21, 2012.

*Primary Examiner* — Robert S Walters, Jr.
(74) *Attorney, Agent, or Firm* — Drinker Biddle & Reath LLP

(57) ABSTRACT

A process for the production of coated textiles comprises the steps of: providing a textile substrate having a first side and a second side opposing the first side; contacting at least a part of the first side of the textile substrate with a spreadable polyurethane mechanical foam; applying a reduced pressure to at least a part of the second side of the textile substrate opposing the first side which has been contacted with the polyurethane mechanical foam; and solidifying the polyurethane mechanical foam with which the textile substrate has been contacted. The invention further relates to a coated textile obtainable by such a process, in particular a synthetic leather.

8 Claims, 1 Drawing Sheet

(51) Int. Cl.
*C07C 227/00* (2006.01)
*C14C 11/00* (2006.01)
*D06M 15/564* (2006.01)
*D06M 23/04* (2006.01)
*C08G 18/66* (2006.01)
*C08G 18/08* (2006.01)
*D06N 3/00* (2006.01)
*C08G 101/00* (2006.01)

(52) U.S. Cl.
CPC .......... *C08G 18/6625* (2013.01); *C14C 11/00* (2013.01); *D06M 15/564* (2013.01); *D06M 23/04* (2013.01); *D06N 3/0045* (2013.01); *D06N 3/0047* (2013.01); *D06N 3/0088* (2013.01); *D06N 3/14* (2013.01); *C08G 2101/0008* (2013.01); *D06N 2211/28* (2013.01); *Y10T 428/249981* (2015.04)

(58) Field of Classification Search
CPC ............... D06N 3/0045; D06N 3/0088; D06N 2211/28; C08G 18/6625; C08G 18/0823; C08G 18/12; C08G 18/3225; C08G 2101/0008; C14C 11/00; Y10T 428/249981

USPC ..................................................... 427/389.9
See application file for complete search history.

(56) References Cited

U.S. PATENT DOCUMENTS

| | | | |
|---|---|---|---|
| 2007/0056118 A1* | 3/2007 | Ellis ..................... | C09D 11/322 8/115.51 |
| 2007/0259984 A1* | 11/2007 | Dorr ................... | C08G 18/0814 521/172 |
| 2007/0270730 A1 | 11/2007 | Rische et al. | |
| 2013/0288551 A1* | 10/2013 | Irnich ................... | D06M 15/05 442/59 |

FOREIGN PATENT DOCUMENTS

| | | |
|---|---|---|
| DE | 2908314 A1 | 9/1979 |
| EP | 0916647 A2 | 5/1999 |
| WO | WO-2007115781 A2 | 10/2007 |

* cited by examiner

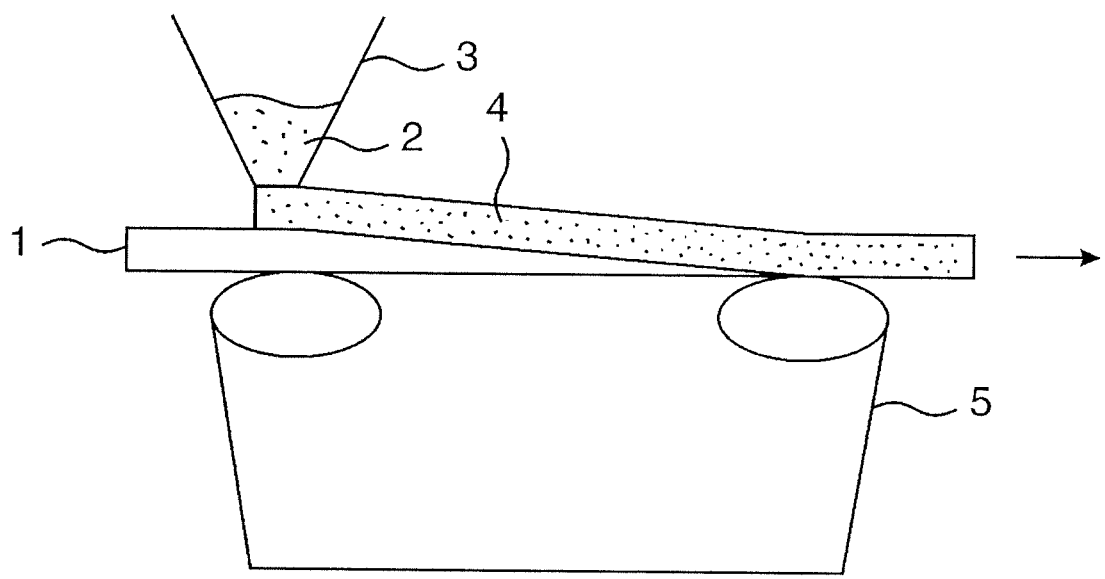

PROCESS FOR THE PRODUCTION OF COATED TEXTILES

CROSS-REFERENCE TO RELATED APPLICATIONS

This application is a national stage application (under 35 U.S.C. §371) of PCT/EP2012/070481, filed Oct. 16, 2012, which claims benefit of Chinese Application No. PCT/CN2011/001754, filed Oct. 21, 2011, both of which are incorporated herein by reference in their entirely.

The present invention relates to a process for the production of coated textiles using reduced pressure. The invention further relates to a coated textile obtainable by such a process, in particular a synthetic leather.

BACKGROUND OF THE INVENTION

The production of synthetic leather by coating textiles with plastics has been known for some time. Synthetic leathers are employed, inter alia, as shoe upper materials, for articles of clothing, as bag-making material or in the upholstery sector, for example. Besides other plastics, such as PVC, the main coating material used here is polyurethane. The generally known principles of coating textiles with polyurethane are described in W. Schröer, Textilveredlung [Textile Finishing] 1987, 22 (12), 459-467. A description of the coagulation process is additionally found in "New Materials Permeable to Water Vapor", Harro Träubel, Springer Verlag, Berlin, Heidelberg, New York, 1999, ISBN 3-540-64946-8, pages 42 to 63.

The main processes used in the production of synthetic leather are the direct coating process, the transfer coating process (indirect coating) and the coagulation (wet) process. In contrast to the direct process, the coating in the transfer process is applied to a temporary support with a subsequent lamination step, in which the film is combined with the textile substrate and detached from the temporary support (release paper). The transfer process is preferably employed with textile substrates which do not permit high tensile stresses during coating, or with open fabrics which are not particularly dense.

In the coagulation process, a textile substrate is usually coated with a solution comprising polyurethane in DMF. In a second step, the coated substrate is passed through DMF/water baths, where the proportion of water is increased stepwise. Precipitation of the polyurethane and formation of a microporous film occur here. Use is made here of the fact that DMF and water have excellent miscibility and DMF and water serve as a solvent/non-solvent pair for polyurethane.

Coagulated polyurethane coatings are employed, in particular, for high-quality synthetic leather, since they have comparatively good breathing activity and a leather feel. The basic principle of the coagulation process is based on the use of a suitable solvent/non-solvent pair for polyurethane. The great advantage of the coagulation process is that microporous, breathing-active synthetic leather having an excellent leather feel can be obtained. Examples are, for example, the synthetic leather brands Clarino® and Alcantara®.

A disadvantage of the coagulation process is the necessity to use large amounts of DMF as an organic solvent. In order to minimize the exposure of employees to DMF emissions during production, additional design measures have to be taken, which represent a not inconsiderable increased outlay compared with simpler processes. Furthermore, it is necessary to dispose of or work up large amounts of DMF/water mixtures. This is problematical since water and DMF form an azeotrope and can therefore only be separated by distillation with increased effort.

In order to avoid the use of DMF, aqueous polyurethane dispersions may be employed. For example, US 2007/0259984 A1 relates to novel microporous coatings based on polyurethane polyurea, and to a process for the production of microporous coatings, in which a composition comprising an aqueous, anionically hydrophilised polyurethane dispersion (I) and a cationic coagulant (II) containing a cationically hydrophilised polyurethane polyurea dispersion is foamed and dried.

Another example for polyurethane dispersion foams is given in WO 2007/115781 A1, describing biomedical foam articles for wounds which are obtained by spraying a polymer dispersion onto a wound. The polymer dispersion is transformed into a three-dimensional molded body which adjusts to the three-dimensional shape of the wound when the polymer dispersion is sprayed onto a surface of the wound and ensures that the wound is entirely dressed in an accurately fitting manner also in the depth dimension in addition to covering the surface of the wound. The biomedical foam articles are reported to be suitable especially for treating chronic wounds.

US 2004/121113 A1 describes a synthetic leather which is made by a impregnating a non-woven or woven textile with an aqueous polyurethane dispersion comprised of a nonionizable polyurethane and an external stabilizing surfactant. The impregnated textile is then exposed to water containing a coagulant for a coagulation time sufficient to coagulate the dispersion. The method may be used to form a synthetic leather having excellent wet ply adhesion and may contain an insoluble multivalent cation organic acid.

In the so-called dipping process a textile is generally dipped into a salt solution, dried, dipped into a polyurethane dispersion paste, dried again, dipped into water and then dried another time. However, this process is laborious due to the large number of steps involved and energy intensive because a considerable amount of water needs to be removed.

It has furthermore been found that in a dipping process the coagulated polyurethane dispersion also resides in the voids between the fibers of the textile. This leads to a hard hand feel of the coated textile which is undesirable in many applications, in particular for synthetic leather production.

The present invention therefore has the object of providing an improved process for the production of coated textiles with fewer steps, a lower energy consumption and without the need for the use of DMF.

According to the present invention this object has been achieved by a process for the production of coated textiles, comprising the steps of:
  providing a textile substrate having a first side and a second side opposing the first side;
  contacting at least a part of the first side of the textile substrate with a spreadable polyurethane mechanical foam;
  applying a reduced pressure to at least a part of the second side of the textile substrate opposing the first side which has been contacted with the polyurethane mechanical foam; and
  solidifying the polyurethane mechanical foam with which the textile substrate has been contacted.

It has surprisingly been found that the foam withstands the reduced pressure treatment in the sense that it does not disintegrate and can be applied onto and into the substrate as a foam. The coated textiles obtained show no polyurethane between the fibers of the textile. This leads to a soft hand feel. Furthermore, up to two dipping and drying steps can be saved with the process according to the invention. Therefore, less energy is consumed in the process.

In a preferred embodiment, the inventively claimed process for the production of coated textiles can be carried out as a continuous process.

Preferably, the polyurethane mechanical foam comprises at least one polyurethane selected from the group comprising cationic hydrophilized polyurethane, anionic hydrophilized polyurethane and nonionic hydrophilized polyurethane.

The textile substrate can preferably be built up from fibers of polyester, nylon (6 or 6,6), cotton, polyester/cotton blends, wool, ramie, spandex, glass. thermoplastic polyurethane (TPU), thermoplastic olefins (TPO) or the like. The textile substrate can be treated with dyes, colorants, pigments, UV absorbers, plasticizers, soil redeposition agents, lubricants, antioxidants, flame inhibitors, rheology agents and the like, either before coating or thereafter, but there is a preference for such additions before coating.

The contacting of the first side of the textile, for example the top side of the textile, with the mechanical foam may be effected by various means such as spraying, doctor blading or pouring from a container.

With respect to the polyurethane mechanical foam, examples for a spreadable foam include foams with a viscosity of ≥0.1 Pa s (20° C.) to ≤5 Pa s (20° C.) determined according to DIN 53019. The spreadable foam may be partially coagulated. The mechanical foam is obtained by mechanical stirring at high speeds, that is to say with the introduction of high shear forces or by expansion of a blowing gas, such as, for example, by blowing in compressed air. The preparation of the mechanical foam can be carried out using any desired mechanical stirring, mixing and dispersing techniques. Air is generally introduced thereby, but nitrogen and other gases can also be used.

The foam density may be in a range of ≥0.5 g/cm$^3$ to ≤1.0 g/cm$^3$, for example.

Aqueous dispersions as basis for the polyurethane mechanical foams are particularly preferred. Generally, the polyurethane polymers present are not particularly restricted as long as they are soluble or dispersible in water, the term "polyurethane" also encompassing polyurethane-polyureas. A review of polyurethane (PUR) dispersions and processes therefore can be found in Rosthauser & Nachtkamp, "Waterborne Polyurethanes, Advances in Urethane Science and Technology", Vol. 10, pages 121-162 (1987). Suitable dispersions are also described, for example, in "Kunststoffhandbuch" [Plastics Handbook]. Vol. 7, 2nd Edition, Hauser, pages 24 to 26.

It is furthermore preferred to employ foam stabilizers in the manufacturing of the mechanical foam. Commercially available foam stabilizers may be used, such as watersoluble fatty acid amides, sulfosuccinamides, hydrocarbon sulfonates or soap-like compounds (fatty acid salts), for example those wherein the lipophilic radical contains from 12 to 24 carbon atoms; in particular alkanesulfonates having from 12 to 22 carbon atoms in the hydrocarbon radical, alkylbenzenesulfonates having from 14 to 24 carbon atoms in the whole of the hydrocarbon radical, or fatty acid amides or soap-like fatty acid salts of fatty acids having from 12 to 24 carbon atoms.

The water-soluble fatty acid amides are preferably fatty acid amides of mono- or di-(C2-3-alkanol)-amines. The soap-like fatty acid salts can be, for example, alkali metal salts, amine salts or unsubstituted ammonium salts. There come into consideration as fatty acids generally known compounds, for example lauric acid, myristic acid, palmitic acid, oleic acid, stearic acid, ricinoleic acid, behenic acid or arachidic acid, or commercial fatty acids, for example coconut fatty acid, tallow fatty acid, soya fatty acid or commercial oleic acid, as well as the hydrogenation products thereof.

The foam stabilizers are advantageously those which do not decompose either under foaming conditions or under application conditions. Preference is given to the use of a mixture of sulfosuccinamides and ammonium stearates. The mixture of sulfosuccinamides and ammonium stearates contains preferably from 20 to 60 wt. % ammonium stearates, particularly preferably from 30 to 50 wt. % ammonium stearates, and preferably from 80 to 40 wt. % sulfosuccinamides, particularly preferably from 70 to 50 wt. % sulfosuccinamides, the percentages by weight being based on the non-volatile components of both foam stabilizer classes and the sum of the wt. % being 100 wt. % in both cases.

Constituent components of aqueous polyurethane dispersions used in accordance with the invention may be the following:

1) Organic di- and/or polyisocyanates, such as, for example, tetramethylene diisocyanate, hexamethylene diisocyanate (HDI), 2-methylpentamethylene diisocyanate, 2,2,4-trimethyl-hexamethylene diisocyanate (THDI), dodecanemethylene diisocyanate, 1,4-diisocyanatocyclohexane, 3-isocyanatomethyl-3,3,5-trimethylcyclohexyl isocyanate (isophorone diisocyanate=IPDI), 4,4'-diisocyanatodicyclohexylmethane (Desmodur® W), 4,4'-diisocyanato-3,3'-dimethyldicyclohexylmethane, 4,4'-diisocyanato-2,2-dicyclohexylpropane, 1,4-diisocyanatobenzene, 2,4- or 2,6-diisocyanatotoluene or mixtures of these isomers, 4,4'-, 2,4- or 2,2'-diisocyanatodiphenylmethane or mixtures of these isomers, 4,4-, 2,4- or 2,2'-diisocyanato-2,2-diphenylpropane-p-xylene diisocyanate and α,α,α',α'-tetramethyl-m- or -p-xylene diisocyanate (TMXDI), and mixtures consisting of these compounds. For the purposes of modification, small amounts of trimers, urethanes, biurets, allophanates or uretdiones of the above-mentioned diisocyanates can be used. MDI, Desmodur W, HDI and/or IPDI are particularly preferred.

2) Polyhydroxyl compounds having 1 to 8, preferably 1.7 to 3.5 hydroxyl groups per molecule and an (average) molecular weight of up to 16,000 g/mol, preferably up to 4000 g/mol. Low-molecular-weight polyhydroxyl compounds defined in each case, such as, for example, ethylene glycol, 1,2-, 1,3-propylene glycol, 1,4-butanediol, 1,6-hexanediol, neopentyl glycol, trimethylolpropane, glycerol, the product of the reaction of 1 hydrazine+2 propylene glycol and oligomeric or polymeric hydroxyl compounds having molecular weights of 350 g/mol to 10,000 g/mol, preferably 840 g/mol to 3000 g/mol, can be considered.

Relatively high-molecular-weight hydroxyl compounds include hydroxypolyesters, hydroxypolyethers, hydroxypolythioethers, hydroxypolyacetates, hydroxypolycarbonates and/or hydroxypolyester amides which are known per se in polyurethane chemistry, preferably those having average molecular weights of 350 g/mol to 4000 g/mol, particularly preferably those having average molecular weights of 840 g/mol to 3000 g/mol. Hydroxypolycarbonates and/or hydroxypolyethers are particularly preferred. When they are used, coagulates having particular stability to hydrolysis can be prepared.

3a) Ionic or potentially ionic hydrophilizing agents containing an acid group and/or an acid group in salt form and at least one isocyanate-reactive group, for example an OH or NH₂ group. Examples are the Na salt of ethylenediamine-β-ethylsulfonic acid (AAS salt solution), dimethylolpropionic acid (DMPA), dimethylolbutyric acid, hydroxypivalic acid or adducts of 1 mol of diamine, preferably isophoronediamine, and 1 mol of an α,β-unsaturated carboxylic acid, preferably acrylic acid.

3b) Nonionic hydrophilizing agents in the form of mono- and/or difunctional polyethylene oxide or polyethylenepropylene oxide alcohols having molecular weights of 300 g/mol to 5000 g/mol. Particular preference is given to monohydroxyl-functional ethylene oxide/propylene oxide polyethers based on n-butanol having 35 to 85% by weight of ethylene oxide units and molecular weights of 900 g/mol to 2500 g/mol. A content of at least 3% by weight, in particular at least 6% by weight, of nonionic hydrophilizing agents is preferred.

4) Blocking agents for isocyanate groups, such as, for example, oximes (acetone oxime, butanone oxime or cyclohexanone oxime), secondary amines (diisopropylamine, dicyclohexylamine), NH-acidic heterocyclic substances (3,5-dimethylpyrazole, imidazole, 1,2,4-triazole), CH-acidic esters (C1-4-alkyl malonates, acetic acid esters) or lactams (ε-caprolactam). Butanone oxime, diisopropylamine and 1,2,4-triazole are particularly preferred.

5) Polyamines as built-in chain extenders. These include, for example, the polyamines discussed under 6). The diamino-functional hydrophilizing agents discussed under 3a) are also suitable as chain extenders to be incorporated.

6) Polyamine crosslinking agents. These are preferably aliphatic or cycloaliphatic diamines, although it is also possible, if needed, to use trifunctional polyamines or polyfunctional polyamines in order to achieve specific properties. In general, it is possible to use polyamines containing additional functional groups, such as, for example, OH groups. The polyamine crosslinking agents, which are not incorporated into the polymer backbone at normal or slightly elevated ambient temperatures, for example 20° C. to 60° C., are either admixed immediately during preparation of the reactive dispersions or at a subsequent point in time. Examples of suitable aliphatic polyamines are ethylenediamine, 1,2- and 1,3-propylenediamine, 1,4-tetramethylenediamine, 1,6-hexamethylenediamine, the isomer mixture of 2,2,4- and 2,4,4-trimethylhexamethylenediamine, 2-methylpentamethylenediamine and diethylenetriamine.

The dispersions may comprise a coagulant. A coagulant is a salt or acid, for example ammonium salts of organic acids, which causes coagulation of the polyurethane under certain conditions, such as, for example, a particular temperature. These substances include an acid-generating chemical agent, i.e. a substance which is not an acid at room temperature, but becomes an acid after warming. Certain examples of such compounds include ethylene glycol diacetate, ethylene glycol formate, diethylene glycol formate, triethyl citrate, monostearyl citrate and an organic acid ester.

The coagulant is preferably present in the composition in an amount of 1% by weight to 10% by weight, based on the solids content of the dispersion.

By applying a reduced pressure to at least a part of the second side of the textile substrate opposing the first side which has been contacted with the polyurethane mechanical foam the mechanical foam is absorbed or sucked into the textile. This may be effected by placing a vacuum chamber under the corresponding section of the textile.

Lastly, the polyurethane mechanical foam with which the textile substrate has been contacted is solidified. Solidification may occur by drying, heating and/or by the action of further coagulants. Examples for further coagulants include salt solutions.

Further embodiments and aspects of the present invention will be described below. They may be combined freely unless the context clearly indicates otherwise.

In one embodiment of the process according to the invention the textile substrate employed is a woven fabric, knitted fabric or nonwoven based on natural and/or synthetic fibers. The textile substrate is particularly preferably a nonwoven (staple fiber nonwoven, microfiber nonwoven or the like).

In another embodiment of the process according to the invention the polyurethane mechanical foam comprises an anionic and/or nonionic hydrophilized polyurethane which is obtainable by A) the preparation of isocyanate-functional prepolymers from
   A1) organic polyisocyanates
   A2) polymeric polyols having number average molecular weights of ≥400 g/mol to ≤8000 g/mol, preferably 400 g/mol to ≤6000 g/mol and particularly preferably ≥600 g/mol to ≤3000 g/mol, and OH functionalities of ≥1.5 to ≤6, preferably ≥1.8 to ≤3, particularly preferably ≥1.9 to ≤2.1, and
   A3) optionally hydroxyl-functional compounds having molecular weights of ≥32 to ≤400 g/mol and
   A4) optionally isocyanate-reactive, anionic or potentially anionic and/or optionally nonionic hydrophilizing agents, B) subsequent reaction of all or some of the free NCO groups thereof
   B1) optionally with amino-functional compounds having molecular weights of ≥32 to ≤400 g/mol and/or
   B2) isocyanate-reactive, preferably amino-functional, anionic or potentially anionic hydrophilizing agents with chain extension, and dispersion of the resultant prepolymers in water before, during or after step B), where any potentially ionic groups present are converted into the ionic form by partial or complete reaction with a neutralizer.

In order to achieve anionic hydrophilization, it is necessary to carry out A4) and/or B2) using hydrophilizing agents which contain at least one group which is reactive to NCO groups, such as amino, hydroxyl or thiol groups, and in addition contain —COO⁻ or —SO₃⁻ or —PO₃²⁻ as anionic groups or fully or partially protonated acid forms thereof as potentially anionic groups.

Preferred aqueous, anionic polyurethane dispersions have a low degree of hydrophilic anionic groups, preferably 0.1 to 15 milliequivalents per 100 g of solid resin.

In order to achieve good sedimentation stability, the number average particle size of the specific polyurethane dispersions is preferably less than 750 nm, particularly preferably less than 500 nm and very particularly preferably less than 400 nm, determined by means of laser correlation spectroscopy.

The ratio of NCO groups in the compounds of component A1) to NCO-reactive groups, such as amino, hydroxyl or thiol groups, in the compounds of components A2) to A4) during preparation of the NCO-functional prepolymer is 1.05 to 3.5, preferably 1.2 to 3.0, particularly preferred 1.3 to 2.5.

The amino-functional compounds in step B) are employed in such an amount that the equivalent ratio of isocyanate-reactive amino groups in these compounds to the free isocyanate groups in the prepolymer is 40 to 150%, preferably between 50 and 125%, particularly preferably between 60 and 120%.

Suitable polyisocyanates of component A1) are the aromatic, araliphatic, aliphatic or cycloaliphatic polyisocyanates having an NCO functionality of 2 which are known per se to the person skilled in the art.

Examples of suitable polyisocyanates of this type are 1,4-butylene diisocyanate, 1,6-hexamethylene diisocyanate (HDI), isophorone diisocyanate (IPDI), 2,2,4- and/or 2,4,4-trimethylhexamethylene diisocyanate, the isomeric bis(4,4'-isocyanatocyclohexyl)methanes or mixtures thereof with any desired isomer content, 1,4-cyclohexylene diisocyanate, 1,4-phenylene diisocyanate, 2,4- and/or 2,6-tolylene diisocyanate, 1,5-naphthylene diisocyanate, 2,2- and/or 2,4'- and/or 4,4'-diphenylmethane diisocyanate, 1,3- and/or 1,4-bis(2-isocyanatoprop-2-yl)benzene (TMXDI), 1,3-bis(isocyanatomethyl)benzene (XDI), and alkyl 2,6-diisocyanatohexanoates (lysine diisocyanates) containing C1-C8-alkyl groups.

Besides the above-mentioned polyisocyanates, it is also possible to employ proportionately modified diisocyanates having a uretdione, isocyanurate, urethane, allophanate, biuret, imino-oxadiazinedione and/or oxadiazinetrione structure and unmodified polyisocyanates containing more than 2 NCO groups per molecule, for example 4.isocyanatomethyloctane 1,8-diisocyanate (nonane triisocyanate) or triphenylmethane 4,4',4"-triisocyanate.

These are preferably polyisocyanates or polyisocyanate mixtures of the above-mentioned type containing exclusively aliphatically and/or cycloaliphatically bonded isocyanate groups and having an average NCO functionality of the mixture of 2 to 4, preferably 2 to 2.6 and particularly preferred 2 to 2.4.

1,6-Hexamethylene diisocyanate, isophorone diisocyanate, the isomeric bis(4,4'-isocyanatocyclohexyl)methanes, and mixtures thereof are particularly preferably employed in A1).

Polymeric polyols having a number average molecular weight $M_n$ of 400 to 8000 g/mol, preferably 400 to 6000 g/mol and particularly preferably 600 to 3000 g/mol, are employed in A2). These preferably have an OH functionality of 1.5 to 6, particularly preferably 1.8 to 3, very particularly preferably 1.9 to 2.1.

Polymeric polyols of this type are the polyester polyols, polyacrylate polyols, polyurethane polyols, polycarbonate polyols, polyether polyols, polyester-polyacrylate polyols, polyurethane polyacrylate polyols, polyurethane polyester polyols, polyurethane polyether polyols, polyurethane polycarbonate polyols and polyester polycarbonate polyols known per se in polyurethane coating technology. They can be employed individually or in any desired mixtures with one another in A2).

Polyester polyols of this type are the polycondensates, known per se, of di- and optionally tri-and tetraols and di- and optionally tri- and tetracarboxylic acids or hydroxycarboxylic acids or lactones. Instead of the free polycarboxylic acids, it is also possible to use the corresponding polycarboxylic anhydrides or corresponding polycarboxylates of lower alcohols for the preparation of the polyesters.

Examples of suitable diols are ethylene glycol, butylene glycol, diethylene glycol, triethylene glycol, polyalkylene glycols, such as polyethylene glycol, furthermore 1,2-propanediol, 1,3-propanediol, 1,3-butanediol, 1,4-butanediol, 1,6-hexanediol and isomers, neopentyl glycol or neopentyl glycol hydroxypivalate, where 1,6-hexanediol and isomers, neopentyl glycol and neopentyl glycol hydroxypivalate are preferred. In addition, it is also possible to employ polyols, such as trimethylolpropane. glycerol, erythritol, pentaerythritol, trimethylolbenzene or trishydroxyethyl isocyanurate.

Dicarboxylic acids which can be employed are phthalic acid, isophthalic acid, terephthalic acid, tetrahydrophthalic acid, hexahydrophthalic acid, cyclohexanedicarboxylic acid, adipic acid, azelaic acid, sebacic acid. glutaric acid, tetrachlorophthalic acid, maleic acid, fumaric acid, itaconic acid, malonic acid, suberic acid, 2-methylsuccinic acid, 3,3-diethylglutaric acid and/or 2,2-dimethylsuccinic acid. The corresponding anhydrides can also be used as acid source.

As long as the average functionality of the polyol to be esterified is >2, monocarboxylic acids, such as benzoic acid and hexanecarboxylic acid, can also be used in addition.

Preferred acids are aliphatic or aromatic acids of the above-mentioned type. Particular preference is given to adipic acid, isophthalic acid and optionally trimellitic acid.

Hydroxycarboxylic acids which can be used concomitantly as reaction participants in the preparation of a polyester polyol containing terminal hydroxyl groups are, for example, hydroxycaproic acid, hydroxybutyric acid, hydroxydecanoic acid, hydroxystearic acid and the like. Suitable lactones are caprolactone, butyrolactone and homologs. Caprolactone is preferred.

Hydroxyl-containing polycarbonates, preferably polycarbonate diols, having number average molecular weights $M_n$ of 400 to 8000 g/mol, preferably 600 to 3000 g/mol, can likewise be employed in A2). These are obtainable by reaction of carbonic acid derivatives, such as diphenyl carbonate, dimethyl carbonate or phosgene, with polyols, preferably diols.

Examples of diols of this type are ethylene glycol, 1,2- and 1,3-propanediol, 1,3- and 1,4-butanediol, 1,6-hexanediol, 1,8-octanediol, neopentyl glycol, 1,4-bishydroxymethylcyclohexane, 2-methyl-1,3-propanediol, 2,2,4-trimethyl-1,3-pentanediol, dipropylene glycol, polypropylene glycols, dibutylene glycol, polybutylene glycols, bisphenol A and lactone-modified diols of the above-mentioned type.

The polycarbonate diol preferably comprises 40 to 100% by weight of hexanediol, preferably 1,6-hexanediol, and/or hexanediol derivatives. Hexanediol derivatives of this type are based on hexanediol and, besides terminal OH groups, contain ester or ether groups. Derivatives of this type are obtainable by reaction of hexanediol with excess caprolactone or by etherification of hexanediol with itself to give di- or trihexylene glycol.

Instead of or in addition to pure polycarbonate diols, it is also possible to employ polyether polycarbonate diols in A2).

The hydroxyl-containing polycarbonates preferably have a linear structure.

Polyether polyols can likewise be employed in A2).

Suitable polyether polyols are, for example, the polytetramethylene glycol polyethers known per se in polyurethane chemistry, as obtainable by polymerization of tetrahydrofuran by means of cationic ring opening.

Likewise suitable polyether polyols are the products, known per se, of the addition of styrene oxide, ethylene oxide, propylene oxide, butylene oxides and/or epichlorohydrine onto di- or polyfunctional starter molecules. Polyether polyols based on the at least proportionate addition of ethylene oxide onto di- or polyfunctional starter molecules can also be employed as component A4) (non-ionic hydrophilizing agents).

Suitable starter molecules which can be employed are all compounds known from the prior art, such as, for example, water, butyl diglycol, glycerol, diethylene glycol, trimethylolpropane, propylene glycol, sorbitol, ethylenediamine, triethanolamine, 1,4-butanediol. Preferred starter molecules are water, ethylene glycol, propylene glycol, 1,4-butanediol, diethylene glycol and butyl diglycol.

Particularly preferred embodiments of the polyurethane dispersions comprise, as component A2), a mixture of polycarbonate polyols and polytetramethylene glycol polyols, where the proportion of polycarbonate polyols in this mixture is 20 to 80% by weight and the proportion of polytetramethylene glycol polyols is 80 to 20% by weight. A proportion of 30 to 75% by weight of polytetramethylene glycol polyols and a proportion of 25 to 70% by weight of polycarbonate polyols are preferred. A proportion of 35 to 70% by weight of polytetramethylene glycol polyols and a proportion of 30 to 65% by weight of polycarbonate polyols are particularly preferred, in each case with the proviso that the sum of the per cent by weight of the polycarbonate polyols and polytetramethylene glycol polyols is 100% and the proportion of the sum of the polycarbonate polyols and polytetramethylene glycol polyether polyols in component A2) is at least 50% by weight, preferably 60% by weight and particularly preferably at least 70% by weight.

The compounds of component A3) have molecular weights of 62 to 400 g/mol.

Polyols in the said molecular weight range having up to 20 carbon atoms, such as ethylene glycol, diethylene glycol, triethylene glycol, 1,2-propanediol, 1,3-propanediol, 1,4-butanediol, 1,3-butylene glycol, cyclohexanediol, 1,4-cyclohexanedimethanol, 1,6-hexanediol, neopentyl glycol, hydroquinone dihydroxyethyl ether, bisphenol A (2,2-bis(4-hydroxyphenyl)propane), hydrogenated bisphenol A (2,2-bis(4-hydroxyclohexyl)propane), trimethylolpropane, glycerol, pentaerythritol, and any desired mixtures thereof with one another, can be employed in A3).

Also suitable are ester diols in the said molecular weight range, such as α-hydroxybutyl-ε-hydroxycaproic acid esters, ω-hydroxyhexyl-γ-hydroxybutyric acid esters, β-hydroxyethyl adipate or β-hydroxyethyl terephthalate.

Furthermore, monofunctional, isocyanate-reactive, hydroxyl-containing compounds can also be employed in A3). Examples of monofunctional compounds of this type are ethanol, n-butanol, ethylene glycol monobutyl ether, diethylene glycol monomethyl ether, ethylene glycol monobutyl ether, diethylene glycol monobutyl ether, propylene glycol monomethyl ether, dipropylene glycol monomethyl ether, tripropylene glycol monomethyl ether, dipropylene glycol monopropyl ether, propylene glycol monobutyl ether, dipropylene glycol monobutyl ether, tripropylene glycol monobutyl ether, 2-ethylhexanol, 1-octanol, 1-dodecanol, 1-hexadecanol.

Preferred compounds of component A3) are 1,6-hexanediol, 1,4-butanediol, neopentyl glycol and trimethylolpropane.

Anionically or potentially anionically hydrophilizing compounds of component A4) are taken to mean all compounds which contain at least one isocyanate-reactive group, such as a hydroxyl group, and at least one functionality, such as, for example, —COO$^-$M$^+$, —SO$^{3-}$M$^+$, —PO(O$^-$M$^+$)$_2$, where M$^+$ is, for example, a metal cation, H$^+$, NH$_4^+$, NHR$_3^+$, where R may in each case be a C1-C12-alkyl, C5-C6-cycloalkyl and/or C2-C4-hydroxyalkyl radical, which enters into a pH-dependent dissociation equilibrium on interaction with aqueous media and may in this way be negatively charged or neutral. Suitable anionically or potentially anionically hydrophilizing compounds are mono- and dihydroxycarboxylic acids, mono- and dihydroxysulfonic acids, and mono- and dihydroxyphosphonic acids, and salts thereof. Examples of anionic or potentially anionic hydrophilizing agents of this type are dimethylolpropionic acid, dimethylolbutyric acid, hydroxypivalic acid, malic acid, citric acid, glycolic acid, lactic acid and the propoxylated adduct of 2-butenediol and NaHSO$_3$, as described in DE-A 2 446 440, pages 5-9, formulae I-III. Preferred anionic or potentially anionic hydrophilizing agents of component A4) are those of the above-mentioned type which contain carboxylate or carboxylic acid groups and/or sulfonate groups.

Particularly preferred anionic or potentially anionic hydrophilizing agents A4) are those which contain carboxylate or carboxylic acid groups as ionic or potentially ionic groups, such as dimethylolpropionic acid, dimethylolbutyric acid and hydroxypivalic acid, or salts thereof.

Suitable nonionically hydrophilizing compounds of component A4) are, for example, polyoxyalkylene ethers which contain at least one hydroxyl or amino group, preferably at least one hydroxyl group.

Examples are the monohydroxyl-functional polyalkylene oxide polyether alcohols containing on statistical average 5 to 70, preferably 7 to 55 ethylene oxide units per molecule, as are accessible in a manner known per se by alkoxylation of suitable starter molecules (for example in Ullmanns Encyclopädie der technischen Chemie [Ullmann's Encyclopedia of Industrial Chemistry], 4th Edition, Volume 19, Verlag Chemie, Weinheim pp. 31-38).

These are either pure polyethylene oxide ethers or mixed polyalkylene oxide ethers, which contain at least 30 mol %, preferably at least 40 mol %, based on all alkylene oxide units present, of ethylene oxide units.

Particularly preferred nonionic compounds are monofunctional mixed polyalkylene oxide polyethers which contain 40 to 100 mol % of ethylene oxide units and 0 to 60 mol % of propylene oxide units.

Suitable starter molecules for nonionic hydrophilizing agents of this type are saturated monoalcohols, such as methanol, ethanol, n-propanol, isopropanol, n-butanol, isobutanol, sec-butanol, the isomeric pentanols, hexanols, octanols and nonanols, n-decanol, n-dodecanol, n-tetradecanol, n-hexadecanol, n-octadecanol, cyclohexanol, the isomeric methylcyclohexanols or hydroxymethylcyclohexane, 3-ethyl-3-hydroxymethyloxetane or tetrahydrofurfuryl alcohol, diethylene glycol monoalkyl ethers, such as, for example, diethylene glycol monobutyl ether, unsaturated alcohols, such as ally alcohol, 1,1-dimethylallyl alcohol or oleyl alcohol, aromatic alcohols, such as phenol, the isomeric cresols or methoxyphenols, araliphatic alcohols, such as benzyl alcohol, anisalcohol or cinnamyl alcohol, secondary monoamines, such as dimethylamine, diethylamine, dipropylamine, diisopropylamine, dibutylamine, bis(2-ethylhexyl)amine, N-methyl- and N-ethylcyclohexylamine or dicyclohexylamine, and heterocyclic secondary amines, such as morpholine, pyrrolidine, piperidine or 1H-pyrazole. Preferred starter molecules are saturated monoalcohols of the above-mentioned type. Diethylene glycol monobutyl ether or n-butanol is particularly preferably used as starter molecule.

Alkylene oxides which are suitable for the alkoxylation reaction are, in particular, ethylene oxide and propylene oxide, which can be employed in any desired sequence or also as a mixture in the alkoxylation reaction.

Di- or polyamines, such as 1,2-ethylenediamine, 1,2- and 1,3-diaminopropane, 1,4-diaminobutane, 1,6-diaminohexane, isophoronediamine, isomer mixture of 2,2,4- and 2,4,4-trimethylhexamethylenediamine, 2-methylpentamethylenediamine, diethylenetriamine, triaminononane, 1,3- and 1,4-xylylenediamine, α,α,α',α'-tetramethyl-1,3- and -1,4- xylylenediamine and 4,4-diaminodicyclohexylmethane and/or dimethylethylenediamine, can be employed as component B1). It is likewise possible to use hydrazine or hydrazides, such as adipohydrazide. Preference is given to isophoronediamine, 1,2-ethylenediamine, 1,4-diaminobutane, hydrazine and diethylenetriamine.

In addition, compounds which, besides a primary amino group, also contain secondary amino groups or, besides an amino group (primary or secondary), also contain OH groups can also be employed as component B1). Examples thereof are primary/secondary amines, such as diethanolamine, 3-amino-1-methylaminopropane, 3-amino-1-ethylaminopropane, 3-amino-1-cyclohexylaminopropane, 3-amino-1-methylaminobutane, and alkanolamines, such as N-aminoethylethanolamine, ethanolamine, 3-aminopropanol, and neopentanolamine.

Furthermore, monofunctional isocyanate-reactive amino compounds, such as, for example, methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl(methyl)aminopropylamine, morpholine, piperidine, or suitable substituted derivatives thereof, amidoamines made from diprimary amines and monocarboxylic acids, monoketimes of diprimary amines, primary/tertiary amines, such as N,N-dimethylaminopropylamine, can also be employed as component B1).

Preferred compounds of component B1) are 1,2-ethylenediamine, 1,4-diaminobutane and isophoronediamine.

Anionically or potentially anionically hydrophilizing compounds of component B2) are taken to mean all compounds which contain at least one isocyanate-reactive group, preferably an amino group, and at least one functionality, such as, for example, —COO$^-$M$^+$, —SO$_3^-$M$^+$, —PO(O$^-$M$^+$)$_2$, where M$^+$ is, for example, a metal cation, H$^+$, NH$_4^+$, NHR$_3^+$, where R may in each case be a C1-C12-alkyl radical, C5-C6-cycloalkyl radical and/or C2-C4-hydroxyalkyl radical, which enters into a pH-dependent dissociation equilibrium on interaction with aqueous media and may in this way be negatively charged or neutral.

Suitable anionically or potentially anionically hydrophilizing compounds are mono- and diaminocarboxylic acids, mono- and diaminosulfonic acids and mono- and diaminophosphonic acids, and salts thereof. Examples of anionic or potentially anionic hydrophilizing agents of this type are N-(2-aminoethyl)-β-alanine, 2-(2-aminoethylamino)-ethanesulfonic acid, ethylenediaminepropyl- or -butylsulfonic acid, 1,2- or 1,3-propylenediamine-β-ethylsulfonic acid, glycine, alanine, taurine, lysine, 3,5-diaminobenzoic acid and the product of the addition reaction of IPDA and acrylic acid (EP-A 0 916 647, Example 1). Furthermore, cyclohexylaminopropanesulfonic acid (CAPA), which is known from WO-A 01/88006, can be used as an anionic or potentially anionic hydrophilizing agent.

Preferred anionic or potentially anionic hydrophilizing agents of component B2) are those of the above-mentioned type which contain carboxylate or carboxylic acid groups and/or sulfonate groups, such as the salts of N-(2-aminoethyl)-β-alanine, of 2-(2-aminoethylamino)ethanesulfonic acid or of the product of the addition reaction of IPDA and acrylic acid (EP-A 0 916 647, Example 1).

The hydrophilization can also be carried out using mixtures of anionic or potentially anionic hydrophilizing agents and nonionic hydrophilizing agents.

In a preferred embodiment for the preparation of the specific polyurethane dispersions, components A1) to A4) and B1) to B2) are employed in the following amounts, where the individual amounts always add up to 100% by weight:

5 to 40% by weight of component A1),
55 to 90% by weight of A2),
0.5 to 20% by weight of the sum of components A3) and B1),
0.1 to 25% by weight of the sum of components A4) and B2), where 0.1 to 5% by weight of anionic or potentially anionic hydrophilizing agents from A4) and/or B2) are used, based on the total amounts of components A1) to A4) and B1) to B2).

In a particularly preferred embodiment for the preparation of the specific polyurethane dispersions, components A1) to A4) and B1) to B2) are employed in the following amounts, where the individual amounts always add up to 100% by weight:

5 to 35% by weight of component A1),
60 to 90% by weight of A2),
0.5 to 15% by weight of the sum of components A3) and B1),
0.1 to 15% by weight of the sum of components A4) and B2), where 0.2 to 4% by weight of anionic or potentially anionic hydrophilizing agents from A4) and/or B2) are used, based on the total amounts of components A1) to A4) and B1) to B2).

In a very particularly preferred embodiment for the preparation of the specific polyurethane dispersions, components A1) to A4) and B1) to B2) are employed in the following amounts, where the individual amounts always add up to 100% by weight:

10 to 30% by weight of component A1),
65 to 85% by weight of A2),
0.5 to 14% by weight of the sum of components A3) and B1),
0.1 to 13.5% by weight of the sum of components A4) and B2), where 0.5 to 3.0% by weight of anionic or potentially anionic hydrophilizing agents from A4) and/or B2) are used, based on the total amounts of components A1) to A4) and B1) to B2).

The preparation of the anionically hydrophilized polyurethane dispersions can be carried out in one or more steps in a homogeneous or multistep reaction, some in the disperse phase. After complete or partial polyaddition from A1) to A4), a dispersion, emulsification or dissolution step is carried out. If desired, a further polyaddition or modification in the disperse phase is subsequently carried out.

All processes known from the prior art, such as, for example, the prepolymer mixing process, acetone process or melt dispersal process, can be used here. The acetone process is preferably used.

For preparation by the acetone process, all or some of constituents A2) to A4) and the polyisocyanate component A1) are usually initially introduced for the preparation of an isocyanate-functional polyurethane prepolymer and optionally diluted with a solvent which is miscible with water, but inert to isocyanate groups and heated to temperatures in the range from 50 to 120° C. In order to accelerate the isocyanate addition reaction, the catalysts known in polyurethane chemistry can be employed.

Suitable solvents are the conventional aliphatic, ketofunctional solvents, such as acetone, 2-butanone, which can be added not only at the beginning of the preparation, but, if desired, can also partly be added later. Preference is given to acetone and 2-butanone.

Other solvents, such as xylene, toluene, cyclohexane, butyl acetate, methoxypropyl acetate, N-methylpyrrolidone, N-ethylpyrrolidone, solvents containing ether or ester units, may additionally be employed and distilled off in full or part or, in the case of N-methylpyrrolidone, N-ethylpyrrolidone, remain completely in the dispersion. However, other solvents apart from the conventional aliphatic, keto-functional solvents are preferably not used.

Any constituents of A1) to A4) which have not yet been added at the beginning of the reaction are subsequently metered in.

In the preparation of the polyurethane prepolymer from A1) to A4), the molar ratio of isocyanate groups to isocyanate-reactive groups is 1.05 to 3.5, preferably 1.2 to 3.0, particularly preferably 1.3 to 2.5.

The conversion of components A1) to A4) into the prepolymer is carried out in part or full, but preferably in full. Thus, polyurethane prepolymers which contain free isocyanate groups are obtained in the solid state or in solution.

In the neutralization step for the partial or complete conversion of potentially anionic groups into anionic groups, bases, such as tertiary amines, for example trialkylamines having 1 to 12 C atoms, preferably 1 to 6 C atoms, particularly preferably 2 to 3 C atoms, in each alkyl radical or alkali metal bases, such as the corresponding hydroxides, are employed.

Examples thereof are trimethylamine, triethylamine, methyldiethylamine, tripropylamine, N-methylmorpholine, methyldiisopropylamine, ethyldiisopropylamine and diisopropylethylamine. The alkyl radicals may also carry, for example, hydroxyl groups, as in the case of the dialkylmonoalkanolamines, alkyldialkanolamines and trialkanolamines. Neutralizers which can be employed, if desired, are also inorganic bases, such as aqueous ammonia solution or sodium hydroxide or potassium hydroxide.

Preference is given to ammonia, triethylamine, triethanolamine, dimethylethanolamine or diisopropylethylamine, as well as sodium hydroxide and potassium hydroxide, particularly preferably sodium hydroxide and potassium hydroxide.

The molar amount of the bases is 50 to 125 mol %, preferably between 70 and 100 mol %, of the molar amount of the acid groups to be neutralized. The neutralization can also be carried out simultaneously with the dispersion if the dispersion water already comprises the neutralizer.

In a further process step, the resultant prepolymer is subsequently dissolved, if this has not already taken place or has only taken place in part, with the aid of aliphatic ketones, such as acetone or 2-butanone.

In the chain extension in step B), $NH_2$- and/or NH-functional components are reacted in part or full with the remaining isocyanate groups of the prepolymer. The chain extension/termination is preferably carried out before the dispersion in water.

For the chain termination, amines B1) containing an isocyanate-reactive group, such as methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl(methyl)aminopropylamine, morpholine, piperidine, or suitable substituted derivatives thereof, amidoamines made from diprimary amines and monocarboxylic acids, monoketimes of diprimary amines, primary/tertiary amines, such as N,N-dimethylaminopropylamine, are usually used.

If the partial or complete chain extension is carried out using anionic or potentially anionic hydrophilizing agents corresponding to definition B2) containing $NH_2$ or NH groups, the chain extension of the prepolymers is preferably carried out before the dispersion.

The aminic components B1) and B2) can optionally be employed in water- or solvent-diluted form in the process according to the invention, individually or in mixtures, where any sequence of addition is in principle possible.

If water or organic solvents are used concomitantly as diluents, the diluent content in the component employed in B) for chain extension is preferably 70 to 95% by weight.

The dispersion is preferably carried out after the chain extension. To this end, the dissolved and chain-extended polyurethane polymer is either introduced into the dispersion water, optionally with high shear, such as, for example, vigorous stirring, or conversely the dispersion water is stirred into the chain-extended polyurethane polymer solutions. The water is preferably added to the dissolved chain-extended polyurethane polymer.

The solvent still present in the dispersions after the dispersion step is usually subsequently removed by distillation. Removal during the dispersion is likewise possible.

The residual content of organic solvents in the polyurethane dispersions is typically less than 1.0% by weight, based on the entire dispersion.

The pH of the polyurethane dispersions is typically less than 9.0, preferably less than 8.5, particularly preferably less than 8.0 and very particularly preferably 6.0 to 7.5.

The solids content of the polyurethane dispersions is 40 to 70% by weight, preferably 50 to 65% by weight, particularly preferably 55 to 65% by weight.

The dispersions may additionally comprise coagulants besides anionically hydrophilized polyurethane.

Said coagulants which can be employed in the are all organic compounds containing at least 2 cationic groups, preferably all known cationic flocculants and precipitants from the prior art, such as cationic homopolymers or copolymers of salts of poly[2-(N,N,N-trimethylamino)ethyl acrylate], of polyethyleneimine, of poly[N-(dimethylaminomethyl)acrylamide], of substituted acrylamides, of substituted methacrylamides, of N-vinylformamide, of N-vinylacetamide, of N-vinylimidazole, of 2-vinylpyridine or of 4-vinylpyridine.

Preferred additional coagulants are cationic copolymers of acrylamide which contain structural units of the general formula (2), particularly preferably cationic copolymers of acrylamide which contain structural units of the formula (1) and those of the general formula (2):

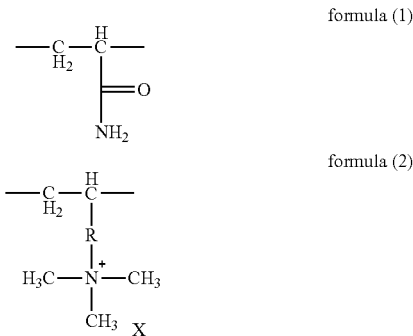

where
R is C=O, —$COO(CH_2)_2$— or —$COO(CH_2)_3$— and
$X^-$ is a halide ion, preferably chloride.

The cationic coagulant employed is particularly preferably a polymer of this type having a number average molecular weight of 500,000 to 50,000,000 g/mol.

Coagulants of this type are marketed, for example, under the trade name Praestol® (Degussa Stockhausen, Krefeld, DE) as flocculants for sewage sludges. Preferred coagulants of the Praestol® type are Praestol® K111L, K122L, K133L, BC 270L, K 144L, K 166L, BC 55L, 185K, 187K, 190K, K222L, K232L, K233L, K234L, K255L, K332L, K 333L, K 334L, E 125, E 150, and mixtures thereof. Very particularly preferred coagulants are Praestol® 185K, 187K and 190K, and mixtures thereof.

In another embodiment of the process according to the invention the polyurethane mechanical foam has a viscosity of ≥5 Pa s (20° C.) to ≤50 Pa s (20° C.) prior to contacting the textile substrate. A preferred range is ≥10 Pa s (20° C.) to ≤40 Pa s (20° C.). The viscosity may be determined using a cone-plate viscometer in accordance with DIN 53019 at a shear rate of 40 $s^{-1}$.

In another embodiment of the process according to the invention the reduced pressure applied to at least a part of the second side of the textile substrate opposing the first side which has been contacted with the polyurethane mechanical foam is from ≥1 mbar to ≤800 mbar. Preferably this pressure is ≥10 mbar to ≤700 mbar and more preferred ≥50 mbar to ≤500 mbar. The choice of the specific pressure depends on the density and viscosity of the spreadable mechanic foam and the desired thickness of polyurethane mechanical foam after solidifying.

In another embodiment of the process according to the invention, solidifying the polyurethane mechanical foam with which the textile substrate has been contacted is effected by heating to a temperature in the range from ≥60° C. to ≤180° C. A preferred temperature range is ≥80° C. to ≤120° C.

In another embodiment of the process according to the invention the polyurethane mechanical foam is applied to at least a part of the first side of the textile substrate with a wet film thickness of ≥10 µm to ≤3000 µm. Preferred wet film thicknesses are ≥10 µm to ≤2000 µm, more preferred ≥10 µm to ≤1000 µm.

In another embodiment of the process according to the invention the process further comprises the step of contacting the textile substrate with a salt solution prior to contacting the at least part of the first side of the textile substrate with the spreadable polyurethane mechanical foam. The salt in the solution may be an organic or inorganic salt. Examples for organic salts are organic onium salts of one or more elements of the fifth main group of the periodic table of the elements.

The salt solution may also comprise modified cellulose such as methylcellulose, ethylcellulose, propylcellulose, hydroxymethylcellulose, hydroxyethylcellulose, hydroxypropylcellulose, hydroxypropylmethylcellulose, carboxymethylcellulose, carboxyethylcellulose and/or carboxypropylcellulose.

The concentration of the salt in the salt solution may, for example, be in a range of ≥10 ppm by weight to ≤10% by weight, based on the total weight of the salt solution.

Preferably the organic onium salt is selected from the group consisting of tertiary ammonium salts, quaternary ammonium salts, tertiary phosphonium salts and quaternary phosphonium salts. In this respect, the tertiary salts are to be understood as tertiary amines or phosphines which have been protonated.

More preferably the organic onium salt is selected from the group consisting of (chloro-hydroxyalkyl)trialkylammonium salts, trialkyl[(trialkoxysilyl)alkyl]ammonium salts, trialkylalkoxyl ammonium salts, trialkylammonium epihydrinamine salts, monoammonium salts of N,N,N',N'-tetrakis (2-hydroxyalkyl)alkylenediamine and diammonium salts of N,N,N',N'-tetrakis(2-hydroxyalkyl)alkylenediamine. Preferred salts of these types are (3-chloro-2-hydroxypropyl) trimethylammonium chloride (CHPTAC), dimethyloctadecyl[3-(trimethoxysilyl)propyl]ammonium chloride, dimethyl octadecyl hydroxyethyl ammonium nitrate, N,N, N-trimethylammonium epihydrineamine salts, N,N,N-triethylammonium epihydrineammonium salts, monoammonium salts of N,N,N',N'-tetrakis(2-hydroxypentyl) ethylenediamine and diammonium salts of N,N,N',N'-tetrakis(2-hydroxypentyl)ethylenediamine.

Examples for inorganic salts are selected from the group consisting of alkali metal salts and alkaline-earth metal salts. The inorganic salt is particularly preferably a salt selected from the group consisting of alkali metal halides, alkali metal nitrates, alkali metal phosphates, alkali metal sulfates, alkali metal carbonates, alkali metal hydrogen carbonates, alkaline-earth metal halides, alkaline-earth metal phosphates, alkaline-earth metal nitrates, alkaline-earth metal sulfates, alkaline-earth metal carbonates and alkaline-earth metal hydrogen carbonates. The inorganic salt is very particularly preferably sodium chloride, potassium chloride, sodium sulfate, sodium carbonate, potassium sulfate. potassium carbonate, sodium hydrogen carbonate, potassium hydrogen carbonate, magnesium chloride, magnesium sulfate, calcium chloride or calcium sulfate. The inorganic salt is still more preferably calcium chloride or magnesium chloride.

Another aspect of the present invention is a coated textile obtainable by a process according to the present invention. In one embodiment the coated textile is synthetic leather.

The present invention will be further described with reference to the following figure without wishing to be limited in any way.

BRIEF DESCRIPTION OF THE DRAWINGS

FIG. 1 schematically shows a process according to the invention

With reference to FIG. 1, a process according to the invention is schematically shown. The top side of a textile substrate 1 is contacted with a liquid polyurethane mechanical foam 2 which is stored in a storage vessel 3. The textile substrate 1 is moved in the direction indicated by the arrow, thus allowing for a continuous production, for example in a roll-to-roll process. The polyurethane mechanical foam forms a layer 4 on the textile substrate 1. Furthermore, textile substrate 1 is passed over vacuum chamber 5. This allows a reduced pressure to be applied to the bottom side of textile substrate 1. By action of the reduced pressure, the layer of liquid polyurethane mechanical foam 4 is at least partially sucked downwards into the textile substrate 1. The polyurethane mechanical foam is then allowed to harden, for example by thermal or by chemical action (not shown). As already mentioned, it is also possible to contact the textile substrate with a salt solution prior to the application of the polyurethane mechanical foam 2 (not shown).

The invention claimed is:

1. A process for the production of coated textiles, comprising the steps of:
providing a textile substrate having a first side and a second side opposing the first side;
contacting the textile substrate with an organic salt solution prior to contacting an at least part of the first side of the textile substrate with a spreadable polyurethane mechanical foam, wherein the organic salt solution comprises an organic onium salt selected from the group consisting of (chloro-hydroxyalkyl)trialkylammonium salts, trialkyl[(trialkoxysilyl)alkyl]ammonium salts, trialkylalkoxyl ammonium salts, trialkylammonium epihydrinamine salts, monoammonium salts of N,N,N',N'-tetrakis(2-hydroxyalkyl)alkylenediamine and diammonium salts of N,N,N',N'-tetrakis(2-hydroxyalkyl)alkylenediamine;

contacting at least a part of the first side of the textile substrate with the spreadable polyurethane mechanical foam, wherein the polyurethane mechanical foam comprises at least one polyurethane selected from the group consisting of cationic hydrophilized polyurethane, anionic hydrophilized polyurethane and nonionic hydrophilized polyurethane;

applying a reduced pressure to at least a part of the second side of the textile substrate opposing the first side which has been contacted with the polyurethane mechanical foam; and solidifying the polyurethane mechanical foam with which the textile substrate has been contacted.

2. The process according to claim 1, wherein the textile substrate employed is a woven fabric, knitted fabric or nonwoven based on natural and/or synthetic fibers.

3. The process according to claim 1, wherein the polyurethane mechanical foam comprises an anionic and/or nonionic hydrophilized polyurethane obtained by A) the preparation of isocyanate-functional prepolymers from
  A1) organic polyisocyanates
  A2) polymeric polyols having number average molecular weights of ≥400 g/mol to ≤8000 g/mol, and OH functionalities of ≥1.5 to ≤6, and
  A3) optionally hydroxyl-functional compounds having molecular weights of ≥32 to ≤400 g/mol and
  A4) optionally isocyanate-reactive, anionic or potentially anionic and/or optionally nonionic hydrophilizing agents, B) subsequent reaction of all or some free NCO groups of the isocyanate-functional prepolymers
  B1) optionally with amino-functional compounds having molecular weights of ≥32 to ≤400 g/mol and/or
  B2) isocyanate-reactive, anionic or potentially anionic hydrophilizing agents, to provide chain-extended pre-polymers, and dispersion of the chain-extended pre-polymers in water, where any potentially ionic groups present are converted into ionic form by partial or complete reaction with a neutralizer.

4. The process according to claim 1, wherein the polyurethane mechanical foam has a viscosity of ≥0.1 Pa s (20° C.) to ≤5 Pa s (20° C.) determined according to DIN 53019 prior to contacting the textile substrate.

5. The process according to claim 1, wherein the reduced pressure applied to at least a part of the second side of the textile substrate opposing the first side which has been contacted with the polyurethane mechanical foam is from ≥1 mbar to ≤800 mbar.

6. The process according to claim 1, wherein solidifying the polyurethane mechanical foam with which the textile substrate has been contacted is effected by heating to a temperature in the range from ≥60° C. to ≤180° C.

7. The process according to claim 1, wherein the polyurethane mechanical foam is applied to at least a part of the first side of the textile substrate with a wet film thickness of ≥10 μm to ≤3000 μm.

8. The process according to claim 1, wherein the salt solution comprises a modified cellulose selected from the group consisting of methylcellulose, ethylcellulose, propylcellulose, hydroxymethylcellulose, hydroxyethylcellulose, hydroxypropylcellulose, hydroxypropylmethylcellulose, carboxymethylcellulose, carboxyethylcellulose, carboxypropylcellulose and mixtures thereof.

* * * * *